US008297661B2

(12) United States Patent
Proulx et al.

(10) Patent No.: US 8,297,661 B2
(45) Date of Patent: Oct. 30, 2012

(54) CONNECTOR FOR FLEXIBLE TUBING

(75) Inventors: Stephen P. Proulx, Boxboro, MA (US);
Joseph Cianciolo, Hudson, NH (US);
Brian Pereira, Salem, NH (US); James Vigna, North Andover, MA (US)

(73) Assignee: EMD Millipore Corporation, Billerica, MA (US)

( * ) Notice: Subject to any disclaimer, the term of this patent is extended or adjusted under 35 U.S.C. 154(b) by 276 days.

(21) Appl. No.: 12/387,912

(22) Filed: May 8, 2009

(65) Prior Publication Data
US 2009/0220294 A1 Sep. 3, 2009

Related U.S. Application Data

(63) Continuation-in-part of application No. 12/082,370, filed on Apr. 10, 2008.

(60) Provisional application No. 61/066,761, filed on Feb. 22, 2008, provisional application No. 60/930,203, filed on May 15, 2007.

(51) Int. Cl.
*F16L 33/00* (2006.01)
(52) U.S. Cl. .......................... 285/242; 29/508
(58) Field of Classification Search .............. 285/242, 285/243, 244, 340, 256; 29/450, 451, 508
See application file for complete search history.

(56) References Cited

U.S. PATENT DOCUMENTS

| 4,451,070 | A | * | 5/1984 | Sauer | 285/242 |
|---|---|---|---|---|---|
| 4,635,973 | A | * | 1/1987 | Sauer | 285/242 |
| 4,723,948 | A | * | 2/1988 | Clark et al. | 285/243 |
| 4,826,477 | A | * | 5/1989 | Adams | 285/242 |
| 4,903,995 | A | * | 2/1990 | Blenkush et al. | 285/255 |
| 4,963,133 | A | * | 10/1990 | Whipple | 285/242 |
| 5,823,580 | A | * | 10/1998 | Ungerecht | 285/242 |
| 5,875,820 | A | * | 3/1999 | Braun | 285/242 |
| 6,000,729 | A | * | 12/1999 | Williamson et al. | 285/242 |
| 6,155,610 | A | * | 12/2000 | Godeau et al. | 285/242 |
| 6,231,085 | B1 | * | 5/2001 | Olson | 285/242 |
| 6,416,085 | B1 | * | 7/2002 | Markovic | 285/242 |
| 6,641,177 | B1 | * | 11/2003 | Pinciaro | 285/242 |
| 6,796,586 | B2 | | 9/2004 | Werth | |
| 7,090,257 | B2 | | 8/2006 | Werth | |
| 7,118,136 | B2 | * | 10/2006 | Ohya | 285/243 |

(Continued)

FOREIGN PATENT DOCUMENTS
EP 1998096 A2 12/2008
(Continued)

OTHER PUBLICATIONS

International Search Report received for PCT Patent Application No. PCT/US2010/001323, mailed on Aug. 30, 2010, 4 pages.

(Continued)

*Primary Examiner* — David E Bochna
(74) *Attorney, Agent, or Firm* — EMD Millipore Corporation

(57) ABSTRACT

A connector is provided for connecting a flexible conduit with a second conduit having a barbed outer surface. The connector accommodates the end of the flexible conduit and the end of the second conduit in a manner which prevents removal of the flexible conduit and the second conduit from the connector. Optionally, the connector has a ring that may be used to apply additional pressure and security to the outer surface of the flexible conduit. additionally, the connector may have a wireless enabled communication and optionally, memory device such as a RFID tag attached or affixed to it.

24 Claims, 13 Drawing Sheets

U.S. PATENT DOCUMENTS 7,370,889 B2 * 5/2008 Maunder et al. ............. 285/242
2005/0082826 A1 4/2005 Werth

FOREIGN PATENT DOCUMENTS

| JP | 2005523406 A | 8/2005 |
| WO | 9724545 A1 | 7/1997 |
| WO | 03/089797 A2 | 10/2003 |
| WO | 03/089797 A3 | 8/2004 |

OTHER PUBLICATIONS

International Preliminary Report on Patentability received for PCT Application No. PCT/US2010/001323, mailed on Nov. 17, 2011, 4 pages.

* cited by examiner

CONNECTOR FOR FLEXIBLE TUBING

CROSS-REFERENCE TO RELATED APPLICATIONS

This application is a Continuation-in-Part Application of U.S. application Ser. No. 12/082,370, filed on Apr. 10, 2008 which claims the benefit of U.S. Provisional Patent Application No. 61/066,761, filed on Feb. 22, 2008 and U.S. Provisional Patent Application No. 60/930,203, filed on May 15, 2007, the entire contents of which are incorporated by reference herein.

FIELD OF THE INVENTION

This invention relates to a connector for connecting flexible tubing to a barbed fitting.

BACKGROUND OF THE INVENTION

Flexible tubing is widely utilized to deliver fluid from a fluid source to a storage site or fluid treatment site. The flexible tubing is connected to the storage volume or fluid treatment site in order to provide the desired fluid delivery. It is necessary to provide a secure and leak proof connection at the end of the flexible tubing in order to avoid fluid contamination and/or leakage. Such a secure connection is particularly required in medical and pharmaceutical applications such as blood pumps, oxygen concentration cartridges, filtration cartridges, intravenous bags or the like.

At the present time, cable ties are utilized to provide a secure connection at the end of the flexible tubing. These cable ties require a tool to tighten the cable tie around the end of the flexible tubing and to cut off the excess cable tie end after the desired tightening is effected. The exposed cut cable tie end is sharp and may cause damage to the storage area, such as a flexible bag or to the fluid treatment site.

U.S. Pat. Nos. 6,796,586 and 7,090,257 as well as patent application publication US 2005/0082826 disclose a lock clamp for flexible tubing. The clamp requires a cumbersome tool to connect the flexible tubing to a barbed fitting.

Accordingly, it would be desirable to provide a connector for connecting a flexible tubing to a barbed fitting which prevents leakage and/or contamination of fluid located within the flexible tubing. In addition, it would be desirable to provide such a connector which remains intact even at elevated fluid pressure within the flexible tubing. Furthermore, it would be desirable to provide such a connector which can be installed by hand without the use of a tool or unusually high hand strength while avoiding the creation of sharp edges. Such a connector would provide ease of installation as well as security against fluid leakage or fluid contamination.

SUMMARY OF THE INVENTION

The present invention provides a connector to connect flexible tubing to a barbed fitting. The connector comprises an annular housing section having a size to accept an open end of a flexible conduit. Flexible fingers are positioned on an outer peripheral surface and/or an inner peripheral surface within the annular housing. The inner peripheral surface comprises one or more tabs. The tabs are sized to contact the step of a barb on a second conduit having an outer barbed surface. The second conduit is positioned within an opening formed by the inner peripheral surface(s) of the annular housing section. The fingers are sized to permit the flexible conduit to be positioned within the annular housing section and to apply pressure to the outside surface and/or inner surface of the flexible conduit. The barbed surface of the second conduit contacts the tab(s) when it is positioned within the opening of the connector. After connection of the flexible conduit to the second conduit is effected with the connector, removal of the flexible conduit from the connector is prevented by the fingers and removal of the second conduit from the connector is prevented by the tab(s).

In one aspect of this invention, a connector is provided having the annular housing section, the opening, the fingers and the tabs as set forth above and including a plate which exerts pressure on the outside surface of the flexible tubing. The plate can be formed in sections and can be formed integrally with the annular housing section or can comprise a separate piece which is joined to the annular housing section.

In another aspect of the present invention, if desired, the connector may be wireless enabled (such as RFID, Bluetooth® or Zigbee® devices) to help track the connector and/or the component to which it is attached.

DESCRIPTION OF SPECIFIC EMBODIMENTS

The connector of this invention is provided with two or more fingers which contact a flexible conduit and which are sufficiently flexible to exert pressure on the flexible conduit when a force is exerted on the flexible conduit to remove the conduit from the connector. The pressure is sufficiently high as to retain the flexible conduit within the connector or to overcome the force exerted on the flexible conduit. The fingers are sufficiently flexible so as to pivot toward the flexible conduit when a pulling force is exerted on the flexible connector which tends to move the flexible conduit out of the connector. The connector of the invention also is provided with at least one tab which fits into the step portion of a barb positioned on the outside surface of a second conduit connected to the flexible conduit through the connector. The at least one tab is sufficiently flexible so that it overrides the barb and then is snap fit into the step at the underside of the barb. It is to be understood that flexible fingers also can be positioned on the tabs thereby to interact with the inner surface of the flexible conduit so as to assist in retaining the flexible conduit within the connector.

Figure 1:
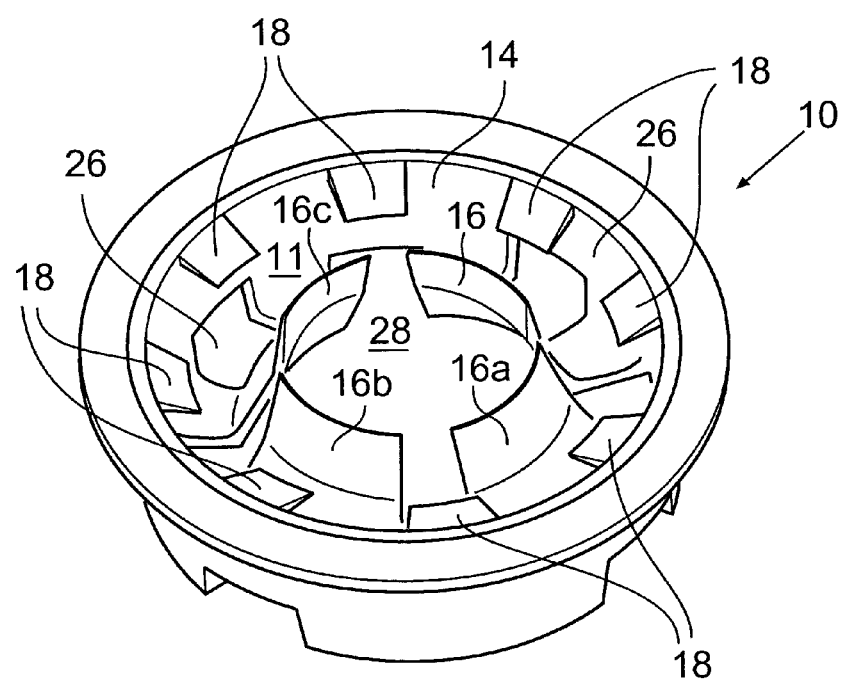
FIG. 1 is a top perspective view of a connector of this invention.
Figure 2:
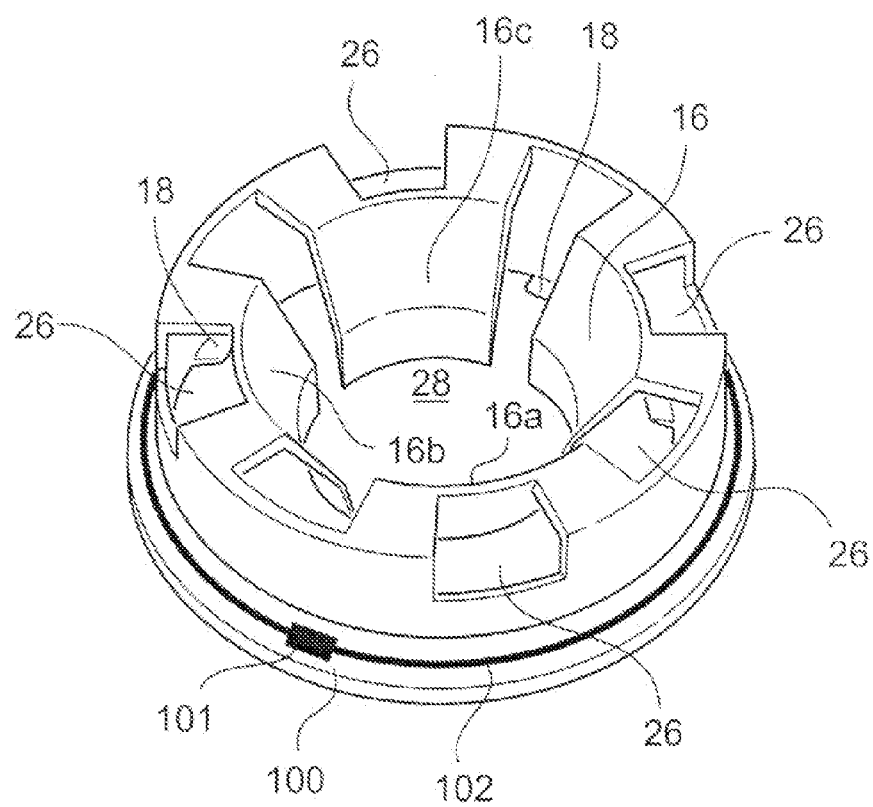
FIG. 2 is a bottom perspective view of the connector of FIG. 1.
Figure 3:
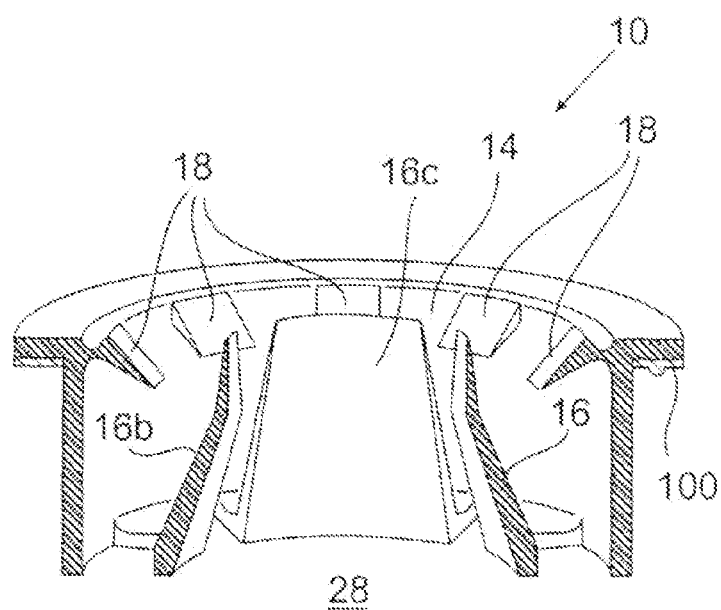
FIG. 3 is a cross sectional view of the connector of FIG. 1.

Referring to FIGS. 1, 2 and 3, the connector 10 of this invention includes an annular housing section 11 formed of outer peripheral wall 14 and the spaced apart plurality of tabs, 16, 16a, 16b and 16c. While the tabs are shown as four tabs, it is to be understood that any number of tabs can be utilized so long as they are sufficiently flexible as to override a barb positioned on the outside surface of a conduit and to snap into position into the step of the barb located at the bottom surface of the barb.

The fingers 18 are attached to the outer peripheral wall 14 and, preferably, extend inwardly from the wall 14 toward the bottom surface 20, (FIG. 2) so as to provide ease of positioning the end of a flexible conduit 22 (FIG. 5) into the annular section 11 of the connector 10. In addition, by extending the finger 18 downwardly, subsequent attempts to remove the flexible conduit 22 from the connector 10 are greatly diminished since the fingers 18 will flex toward the flexible conduit 22, thereby directly exerting pressure on the outside surface 24 of the flexible conduit 22 and thereby to cause the flexible conduit 22 to be retained within the connector 10. The fingers 18 can be the same length or different lengths. For example, when eight fingers 18 are employed every other finger can be the right length for a thin wall conduit and the others having an appropriate length for a thick wall conduit. Any number of fingers 18 can be used of one or more lengths so long as they are sufficient in number and length to grasp and hold the flexible conduit 22 as desired.

The connector 10 is optionally provided with spaced-apart openings 26 to increase the flexibility of the annular housing section 11 thereby to improve the ease of positioning the flexible conduit 22 into the connector 10. The hollow inner pathway 28 of the connector 10 is provided to permit the insertion of the second conduit 30 having the barb 32 having a step 34 and a bottom surface 36 (FIG. 5), into which tabs 16, 16a, 16b and 16c are positioned (FIGS. 1 and 5), and to allow for liquid or gas to pass between the flexible conduit 22 and the second conduit 30.

Optionally, the connector 10 may be wirelessly enabled as shown in FIG. 2 and other Figures described below. The wireless communications device 100 maybe a RFID tag having a communication and storage or memory component 101 and an antenna 102 as shown or other wireless devices such as Bluetooth® or Zigbee® wireless enabled communications devices.

By wirelessly enabling the connector 10 one can track the history of the connector and/or the component to which it is attached. For example, with a read only wireless device one can track the manufacture of the connector such as the lot number, date of manufacture and the like. With a read/write device containing an active memory, one can also add information to the wireless device such as when the connector was placed on the component, what the component is to which the device 100 is attached, what the component is meant to be used with, one or more trackable events that occur to the connector and the component to which it is attached such as sterilization, warehousing, use and the like.

Optionally, the wireless device may be gamma radiation stable such that the device is not damaged or destroyed due to the radiation typically used in many sterilization processes. Such devices are known as FRAM RFID and can have a storage component that employs a non-charge based storage mechanism such as a ferro-magnetic or magnetoresistive memory storage device.

The wireless device 100 may attached to the connector by a mechanical device such as by a rivet or screw or a strap under a top surface of the connector and passing through two of the openings 26 and then to the wireless device (not shown) or it 100 can be molded into the connector 10 (as in FIGS. 7 and 11) or it 100 can be formed on or adhered to the surface of the connector 10 as shown in FIGS. 2, 3, 5 and 6.

Figure 4:
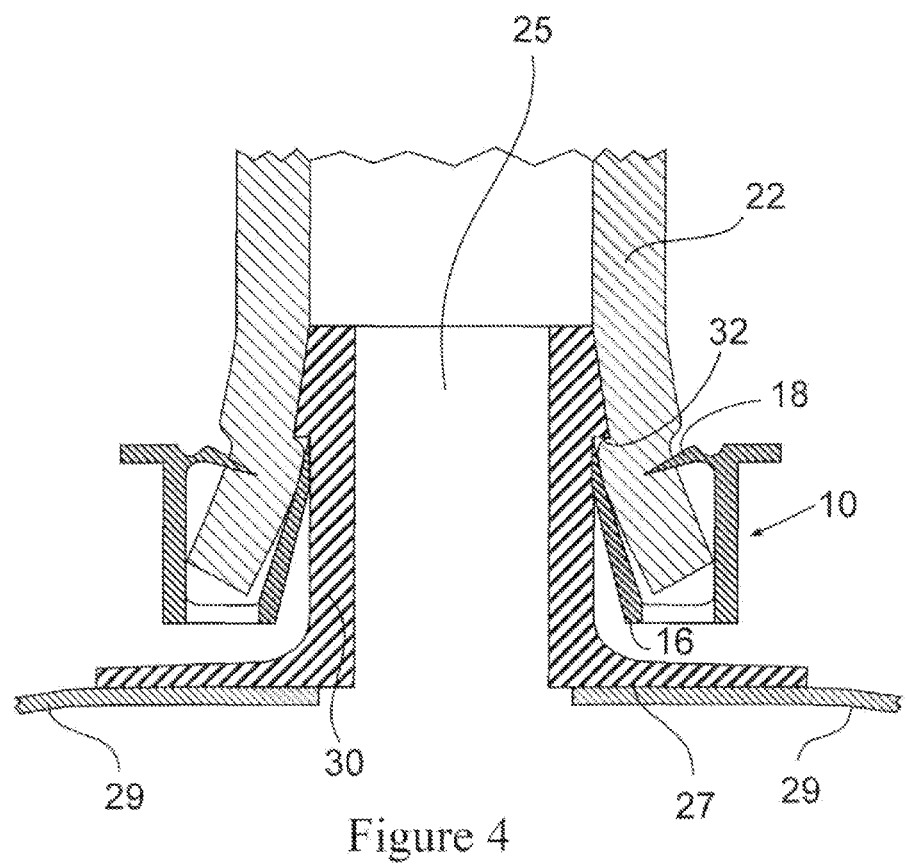
FIG. 4 is a perspective view of a barbed conduit.

As shown in FIG. 4, a barbed second conduit 30 includes a barb 32 and an opening 25 that permits fluid flow therethrough. The conduit section 30 is attached to a flange 27 which, in turn, is attached to a fluid processor 29 which can retain fluid such as a bag or can effect a unit operation such as a filtration cartridge.

Figure 5:
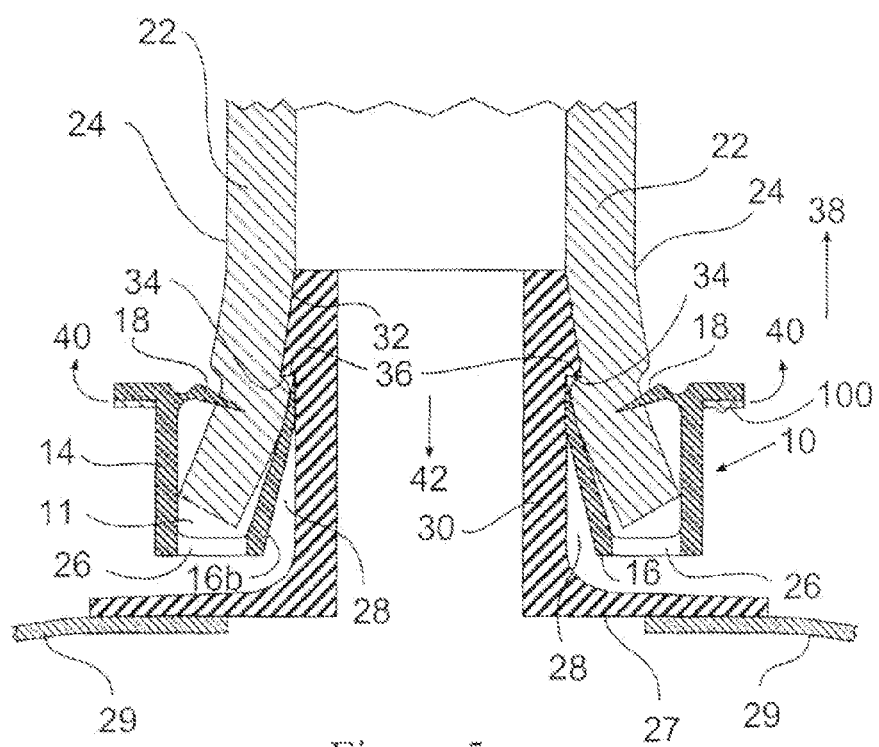
FIG. 5 is a cross sectional view of the connector of FIGS. 1-3 with a flexible conduit and a barbed second conduit positioned within the connector.

As shown in FIG. 5, the fingers 18 exert pressure on the outside surface 24 of flexible conduit 22. When a pulling force exemplified by arrow 38 is exerted on conduit 22, the fingers 18 pivot in the direction exemplified by arrows 40 thereby compressing the outside surface 24 of the flexible conduit 22, causing the flexible conduit 22 to be retained within the connector 10.

When a pulling force, as exemplified by arrow 42 is exerted on conduit 30, the tabs 16, 16a, 16b, and 16c exert a counter force on the bottom surface 36 of barb 32, thereby to effect retention of the conduit 30 in connector 10. Thus, the fingers 18 and tabs 16, 16a, 16b and 16c work in concert to retain the flexible conduit 22 and/or conduit 30 in the connector 10 when a pulling force is exerted on the flexible conduit 22 and top conduit 30. In addition, the positioning of conduit 22 and conduit 30 in connector 10 can be effected by hand without the need for a tool. Furthermore, the connector 10 can be sized to accept a wide size range of flexible conduits and second conduits having a barbed outer surface by providing a size range of connectors 10 having a variety of sizes of annular housing sections 11 and a variety of sizes of holes 28.

The conduit 22 has a flexibility sufficient to permit the fingers 18 to exert a pressure thereon when a force is exerted on the flexible conduit 22 in a direction to pull the flexible conduit 22 from the connector 10. Representative suitable flexible connectors can be made from silicone, preferably platinum cured silicone; polyethylene, propropylene; polyvinyl chloride; a thermoplastic elastomer; PTFE resin; EPDM, C-Flex® resin available from Consolidated Polymer Technologies of Clearwater Fla. or the like. The flexible tubing may also have a protective/pressure resistive braid over them or incorporated as a jacket onto them. Such braids are well known and can be made of polyester, polypropylene or stainless steel.

The barbed conduit 30 can be made of any material such as a polymeric composition, or a metal composition such as stainless steel so long as the tabs 16, 16a, 16b and 16c can be positioned on the bottom surface 36 of the barb 34 when the barbed conduit 30 is inserted in hole 28.

Figure 6:
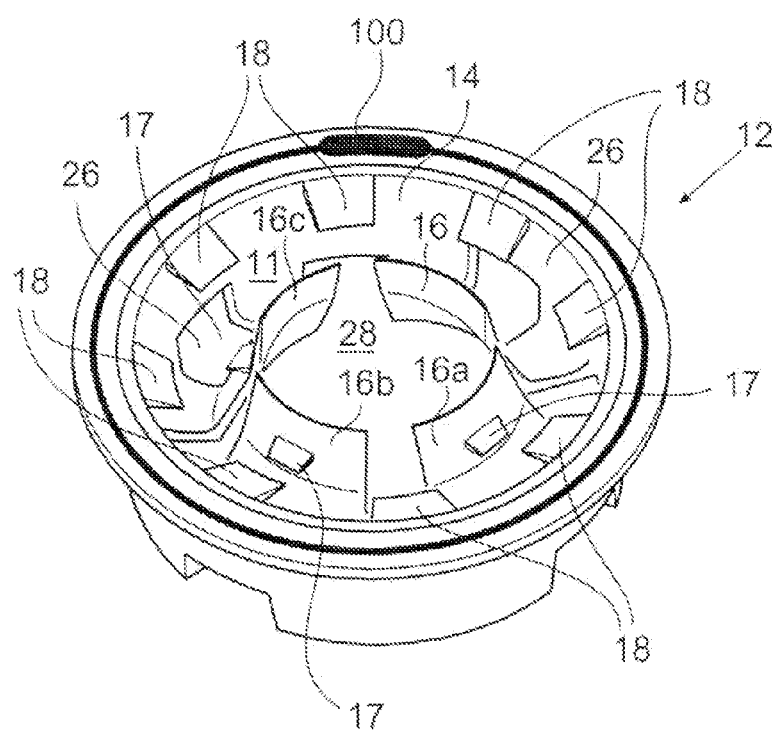
FIG. 6 is a perspective view of an alternative connector of this invention.

Referring to FIG. 6, an alternative connector 12 of this invention is shown. The connector 12 has the same elements of the connector 10 of FIG. 1 wherein like indicia identify like elements. The connector 12 includes a second set of fingers 17 which are positioned on the tabs 16, 16a, 16b and 16c. The fingers 17 function in the same manner as fingers 18 as described above. It is to be understood that the connector can be formed with only fingers 17, without fingers 18.

Figure 7:
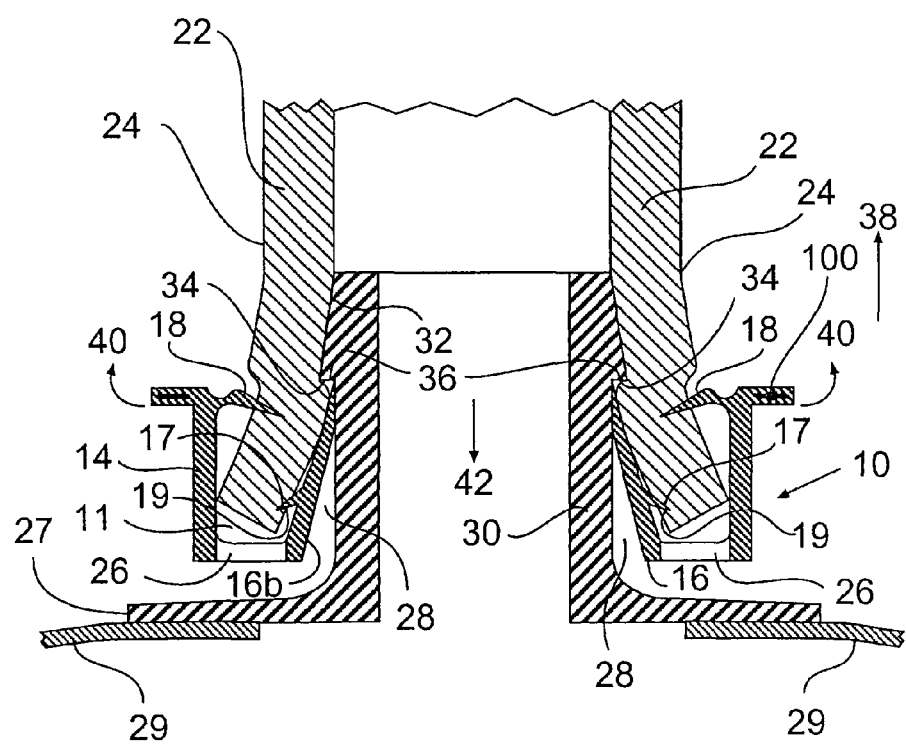
FIG. 7 is a cross sectional view of the connector of FIG. 6 with a flexible conduit and a barbed second conduit positioned within the connector.

As shown in FIG. 7, the fingers 18 exert pressure on the outside surface 24 of flexible conduit 22 and the fingers 17 exert pressure on the inside surface 19 of flexible conduit 22. When a pulling force exemplified by arrow 38 is exerted on conduit 22, the fingers 17 and 18 pivot in the direction exemplified by arrows 40 thereby compressing the outside surface 24 and the inside surface 19 of the flexible conduit 22, causing the flexible conduit 22 to be retained within the connector 10.

When a pulling force, as exemplified by arrow 42 is exerted on conduit 30, the tabs 16, 16a, 16b, and 16c exert a counter force on the bottom surface 34 of barb 32, thereby to effect retention of the conduit 30 in connector 10. Thus, the fingers 17 and 18 and tabs 16, 16a, 16b and 16c work in concert to retain the flexible conduit 22 and/or conduit 30 in the connector 10 when a pulling force is exerted on the flexible conduit 22 and second conduit 30. The positioning of flexible conduit 22 and second conduit 30 in connector 10 can be effected by hand without the need for a tool. Furthermore, the connector 10 can be sized to accept a wide size range of flexible conduits and second conduits having a barbed outer surface by providing a size range of connectors 10 having a variety of sizes of annular housing sections 11 and a variety of sizes of holes 28.

Referring to FIGS. 5 and 7, in use, the barbed second conduit 30 is inserted into inner pathway 28 so that the barb 34 is positioned on the top of tabs 16a, 16b and 16c (FIGS. 1 and 6). The flexible conduit 22 then is inserted into annular housing section 11 to an extent such that its bottom end by-passes both sets of fingers 17 and 18. The flexible conduit 22 and second conduit 30 are thus retained within the connector 10 or 12 in the manner described above.

Figure 8:
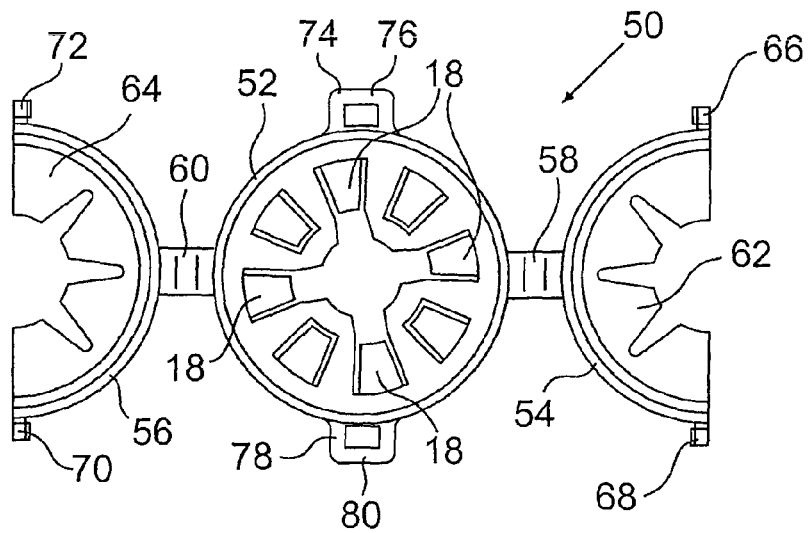
FIG. 8 is a top view of a connector of this invention having hinged plate sections.
Figure 9:
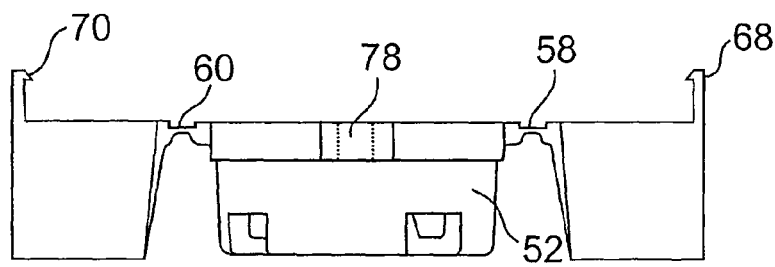
FIG. 9 is a side view of the connectors of FIG. 8.
Figure 10:
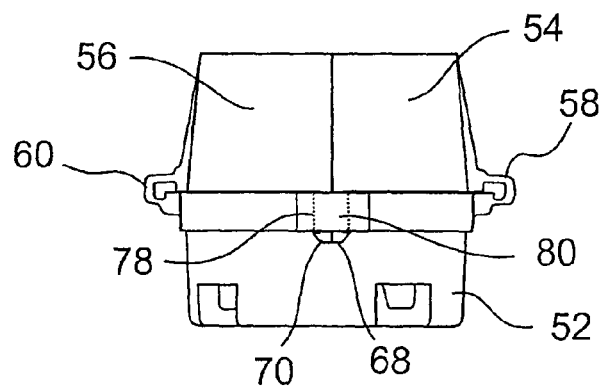
FIG. 10 is a side view of the connector of FIG. 9 having the plate sections closed.

Referring to FIGS. 8, 9 and 10, a connector of this invention 50 includes a connector section 52 and two plate sections 54 and 56. The plate sections 54 and 56 are joined to connector section 52 by living hinges 58 and 60. The hinges 58 and 60 permit moving the plate sections 54 and 56 into locked contact with the connector section 52. After the flexible conduit such as flexible conduit 22 (FIG. 5) is positioned within the connector section 52 as described above with reference to FIG. 5, the plate sections 54 and 56 are pivoted about hinges 58 and 60. The hinges 58 and 60 function to expose the inner surface of the connector section 52 so that an end of a flexible conduit can be inserted therein. The hinges 58 and 60 also permit the plate sections 54 and 56 to be positioned in contact with an outside surface of a flexible conduit positioned within connector section 52 thereby to assist in preventing removal of the flexible conduit from the connector section 52. The plate sections 54 and 56 are locked into position against the outside surface of the flexible conduit 22 (FIG. 6) so that the inside surfaces 62 and 64 press against the outside surface 24 of conduit 22 (FIG. 5). It is to be understood that surfaces 62 and 64 can be smooth or rough such as serrated or having prongs extended there from to provide a gripping force on the flexible conduit. Locking is effected, for example, by means of tabs 66, 68, 70 and 72 which lock into the walls of openings 74, 76, 78 and 80. It is to be understood that locking of the plate sections 54 and 56 to connection section 52 can be effected by any conventional means. It is to be understood that more than two hinged plate sections can be utilized such as three or four plate sections. It is also to be understood that the plate sections 54 and 56 can be pivotally connected to the connector section 52 by any conventional means such as plastic ties which extend through openings shaped like openings 74, 76, 78 and 80.

Figure 11:
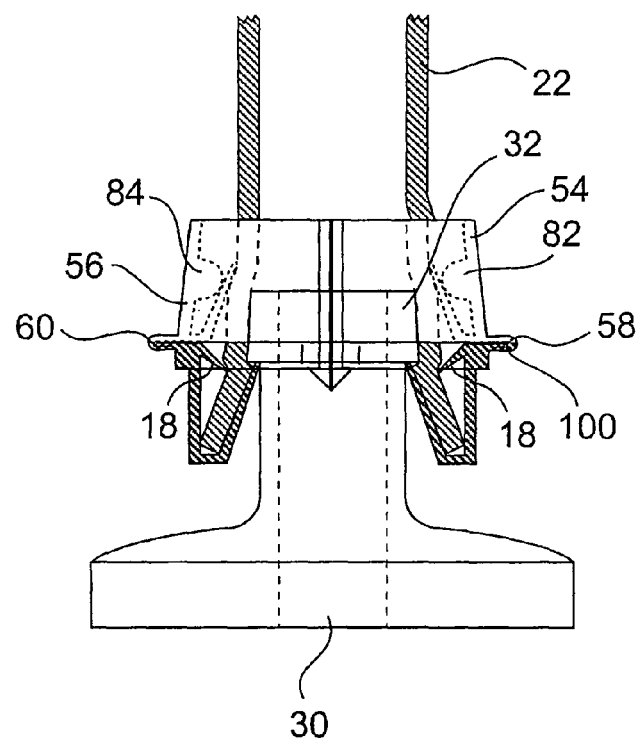
FIG. 11 is a side partial cross sectional view of the connector of FIGS. 8, 9 and 10 positioned on a flexible conduit and on a barb and modified with an extended surface on the plate sections.

As shown in FIG. 11, the connector of FIGS. 8, 9 and 10 can be modified so that the inside surfaces of the plate sections 54 and 56 include bead shaped extended surfaces 82 and 84. The purpose of the extended surfaces 82 and 84 is to exert a compressive force on flexible conduit 22 against barb 32.

Figure 12:
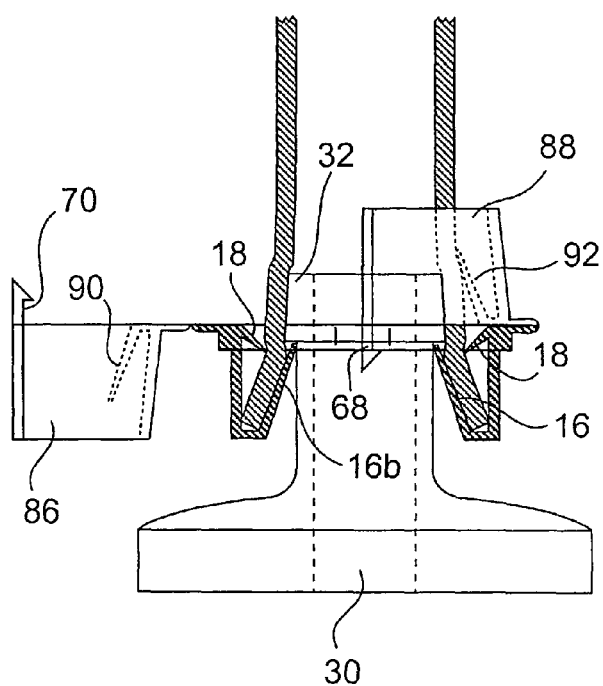
FIG. 12 is a side partial cross sectional view of an alternative embodiment of this invention having plate sections.

Referring to FIG. 12, one alternative connector of this invention is shown in position on a barbed conduit. The tabs 16 and 16b function in the same manner as described above with reference to FIGS. 1, 2 and 3. The plate sections 86 and 88 are provided with flexible caps 90 and 92. The flexible caps 90 and 92 provide flexibility for accommodating various sized flexible conduits that are positioned with the barbed conduit 30 in the manner described above (FIG. 5).

Figure 13:
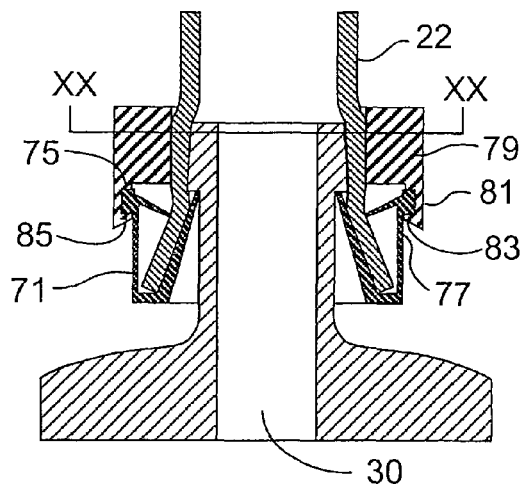
FIG. 13 is a cross sectional view of a two piece connector of this invention positioned on a flexible conduit.
Figure 13A:
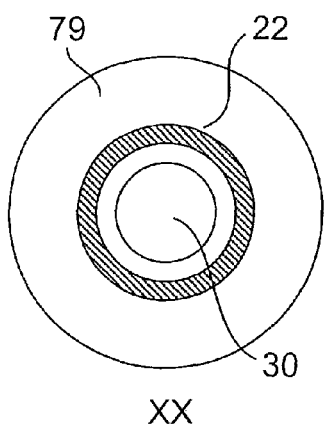
FIG. 13a is a top-down cross sectional view of FIG. 13 along lines XX to XX.

Referring to FIG. 13, a two piece connector of this invention is shown. The connector section 71 is the same as connector 10 (FIG. 1) except that it includes, on its outside surface a plurality of slots, at least two, preferably three or more, such as four slots 73 on its top surface 75 as shown. The slots 73 communicate with a circular path 77 that extends around at least a portion of the circumference of connector section 71. A second piece of this connector comprises a ring 79 which includes prongs 81 having a step 83 which fits below lip 85 of connector section 71. In use, the ring 79 is positioned on the flexible conduit 22. The end of the flexible conduit is placed in the connector section 71 in the manner described above with reference to connector 10 of FIG. 5. The ring 79 then is moved into the connector section 71 by positioning the prongs 81 into the slots 73 so that the steps 83 are positioned below lip 85. The ring 79 then is rotated in circular path 77 so that the ring 79 is prevented from separating from connector section 71 by the mating lip 85 and steps 83. It is to be understood that ring 79 and connector piece 71 can be connected to each other by any conventional means such as by being snap fit together or secured to each other with conventional mating helical paths.

Figure 14:
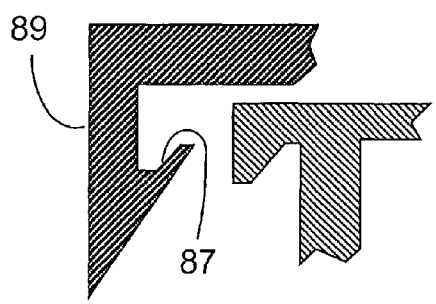
FIG. 14 is a partial cross sectional view of an alternative configuration for a two piece connector of this invention.
Figure 15:
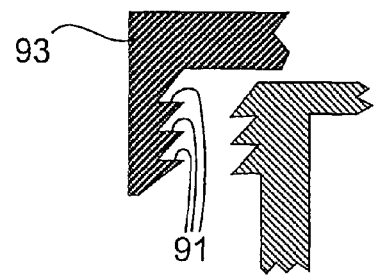
FIG. 15 is a partial cross sectional view of an alternative configuration of a two piece connector of this invention.

As shown in FIG. 14, the steps on the prongs 89 can be angled. As shown in FIGS. 15, a plurality of angled steps 91 can be utilized on each prong 93. Any geometry which promotes retention of the ring and connector section of the two piece connector of this invention can be utilized herein.

Figure 16:
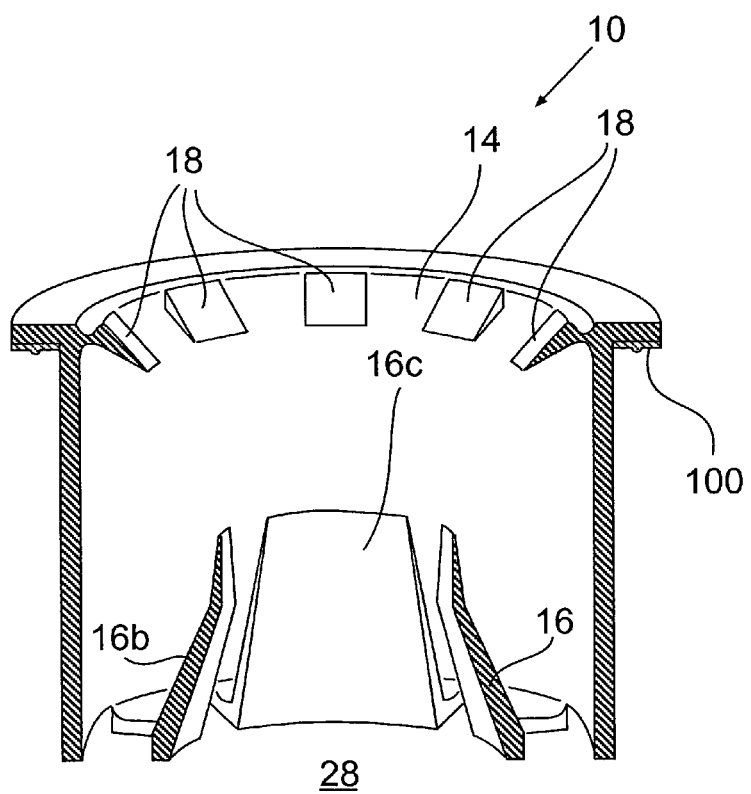
FIG. 16 is a partial cross sectional view of an alternative configuration of a one piece connector of this invention
Figure 17:
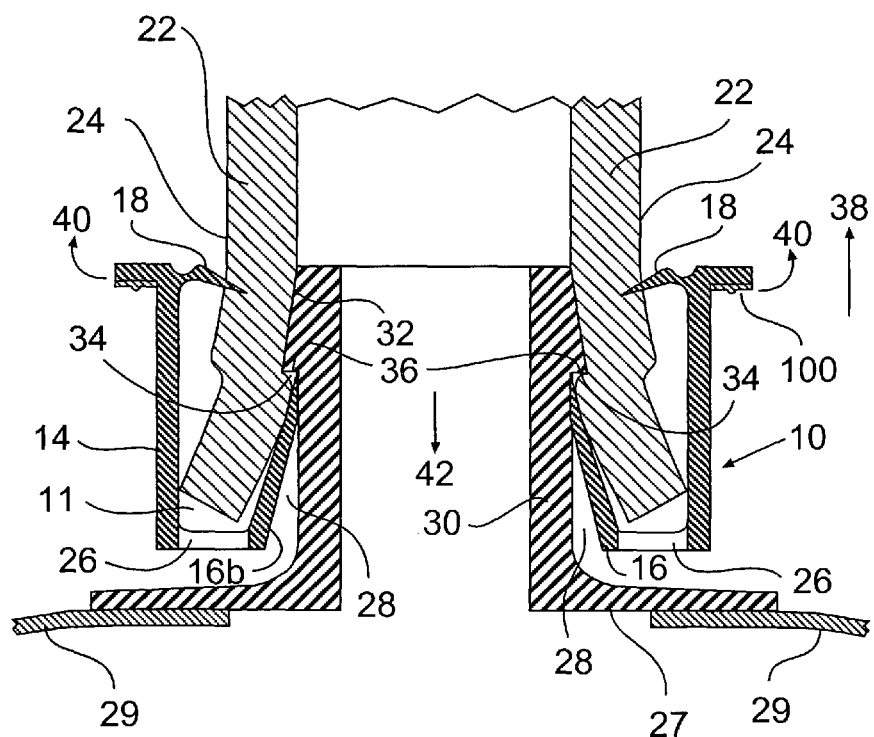
FIG. 17 is a partial cross sectional view of an alternative configuration of a one piece connector on barbed conduit of this invention

FIGS. 16 and 17 show another embodiment of the present invention similar to that of FIGS. 1-3 and 5. In this embodiment, the length of the outer peripheral wall 14 is of a length such that when the connector 10 is attached to a flexible conduit 22 and second conduit 30, the fingers 18 are spaced apart from the tabs 16 and exert pressure on the outside surface 24 of the flexible conduit 22 along an outer surface portion of the tapered barb 32 of the second conduit 30. Preferably, the fingers exert their pressure somewhere between 10% up the length of the outer surface of barb 32 to about 90% of the length of the outer surface of the barb 32 as measured from the step 34 of the barb 32. More preferably the fingers exert their pressure somewhere between about 20% up the length of the outer surface of barb 32 to about 80% of the length of the outer surface of the barb 32 as measured from the step 34 of the barb 32 or the fingers exert their pressure somewhere between about 25% up the length of the outer surface of barb 32 to about 75% of the length of the outer surface of the barb 32 as measured from the step 34 of the barb 32. Most preferably the fingers exert their pressure at about halfway up the length of the outer surface of barb 32 as measured from the step 34 of the barb 32.

What is claimed:

1. A connector system for a flexible conduit and a second conduit comprising a flexible conduit having a hollow inner pathway therethrough, a second conduit having a barbed outer surface with a step part and a bottom part and an opening between the bottom part and a farthermost portion of the barb from the bottom part, the second conduit barb portion being inserted within the inner hollow pathway of the flexible conduit, a connector for said flexible conduit and second conduit, the connector having a central annular opening through which the flexible conduit and barbed portion of the second conduit can be inserted, one or more tabs sized to contact the step part of the barb and to contact an inner surface of the flexible conduit and one or more flexible fingers sized to contact an outer surface of the flexible conduit.

2. The connector system of claim 1 wherein the fingers interact with the flexible conduit between about 10% of a length of the barbed outer surface of the second conduit to about 90% of the length of the barbed outer surface of the second conduit as measured from the step part of the second conduit.

3. The connector system of claim 1 wherein the fingers interact with the flexible conduit between about 20% of a length of the barbed outer surface of the second conduit to about 80% of the length of the barbed outer surface of the second conduit as measured from the step part of the second conduit.

4. The connector system of claim 1 wherein the fingers interact with the flexible conduit between about 25% of a length of the barbed outer surface of the second conduit to about 75% of the length of the barbed outer surface of the second conduit as measured from the step part of the second conduit.

5. The connector system of claim 1 wherein the fingers interact with the flexible conduit about halfway of a length of the barbed outer surface of the second conduit as measured from the step part of the second conduit.

6. A connector comprising:
(i) an annular housing having an outer peripheral surface and an inner peripheral surface, the inner peripheral surface being of a size to accept an open end of a flexible conduit;
(ii) a plurality of flexible fingers positioned on the outer peripheral surface of the annular housing; and
(ii) one or more tabs on an inner peripheral surface of the annular housing,
wherein the tabs are sized to contact a step of a barb on a second conduit having a barbed outer surface and to contact an inner surface of the flexible conduit and the fingers are sized to permit the flexible conduit to be positioned within the annular housing, wherein the connector connects the the flexible conduit and the second conduit having a barbed outer surface.

7. A connector of claim 6, wherein the fingers exert a compressive force on an outer surface of the flexible conduit.

8. The connector of claim 6, wherein the tabs exert a compressive force on an inner surface of said flexible conduit.

9. The connector of claim 6 wherein said one or more flexible fingers for exerting a compressive force on an outer surface of said flexible conduit includes a detachable ring.

10. The connector of claim 6 wherein said one or more flexible fingers for exerting a compressive force on an outer surface of said flexible conduit includes hinged plate sections.

11. The connector of claim 6 wherein said connector includes a hinged plate section capable of exerting a compressive force on an outer surface of said flexible conduit.

12. The connector of claim 6, further comprising a wireless enabled communication and memory device.

13. The connector of claim 6 further comprising a wireless enabled communication and a memory device, wherein the wireless communication and memory device is selected from the group consisting of a RFID tag, a Bluetooh device and a Zigbee device.

14. The connector of claim 6 further comprising a wireless enabled communication and memory device and wherein the wireless enabled communication and memory device is attached to the connector by a means selected from the group consisting of mechanical, adhesive and thermal bonding means.

15. The connector of claim 6 further comprising a wireless enabled communication and memory device and wherein the wireless enabled communication and memory device is molded onto or into one of the surfaces of the connector.

16. The connector of claim 6 further comprising a wireless enabled communication and memory device and wherein the wireless enabled communication and memory device has read/write capability.

17. The connector of claim 6 further comprising a wireless enabled communication and memory device and wherein the wireless enabled communication and memory device has read/write capability and tracks one or more events occurring to the connector and/or a component to which it is connected.

18. A connector system for transporting fluid wherein the connector system comprises, a flexible conduit, a second conduit having a barbed outer surface and a connector for connecting said flexible conduit and said second conduit having a barbed outer surface, wherein said connector comprises an annular housing having an outer peripheral surface and an inner peripheral surface, the inner peripheral surface being of a size to accept an open end of a flexible conduit, a plurality of flexible fingers on the outer peripheral surface of the annular housing and one or more tabs on the inner peripheral surface of the annular housing, wherein the tabs secure the second conduit within the connector by exerting a force on a bottom surface of the barbed outer surface, wherein the tabs are sized to contact a step of a barb on the second conduit and to contact an inner surface of the flexible conduit, thereby to exert a compressive force on the inner surface of the flexible conduit, and the fingers exert a compressive force on an outer surface of said flexible conduit, wherein fluid is transported between the flexible conduit and the second conduit having a barbed outer surface.

19. A connector system for transporting fluid, wherein the connector system comprises a flexible conduit having a hollow inner pathway therethrough, a second conduit having a barbed outer surface with a step part and a bottom part, a flange portion adjacent the barbed outer surface and an opening between the flange and the farthermost portion of the barb, the second conduit barb portion being inserted within the inner hollow pathway of the flexible conduit, a connector for said flexible conduit and second conduit, the connector having a central annular opening through which the flexible conduit and barbed portion of the second conduit can be inserted, one or more flexible tabs outside of and adjacent to the central annular opening and capable of interacting with the step part and bottom part of the barbed section and capable of contacting the inner hollow pathway of the flexible conduit , and one or more flexible fingers arranged outside of and adjacent to the one or more tabs to interact with an outer surface of the flexible conduit, wherein fluid is transported between the flexible conduit and the second conduit.

20. The connector of claim 19, further comprising second one or more fingers which extend from an outer surface of the one or more tabs and the second one or more fingers are capable of interacting with an inner surface of the flexible conduit.

21. The connector system of claim 19 wherein said connector includes a hinged plate section capable of exerting a compressive force on an outer surface of said flexible conduit.

22. A process of securing a flexible conduit to a second conduit comprising the steps of providing a flexible conduit having an outer wall and an inner pathway therethrough, a second conduit having a flange portion and an outer barbed portion extending away from at least one side of the flange portion, the barbed portion having a step part and a bottom part, the second conduit having a first opening in the flange portion and a second opening in the barbed portion with a bore between the first and second openings, providing a connector formed of a central opening having an inner diameter that is greater to or equal to the outer diameter of the flexible conduit, and having one or more flexible fingers arranged outside of and adjacent to one or more tabs, inserting the barbed portion of the second conduit into the inner pathway of the flexible conduit so as to cause the one or more tabs to interact with the barbed portion of the second conduit and the one or more tabs to contact the inner pathway of the flexible conduit and the one or more flexible fingers to interact with a surface of the flexible conduit to produce a strong seal between the second conduit, the connector and the flexible conduit.

23. The process of claim 22 wherein said connector includes a detachable ring capable of exerting a compressive force on an outer surface of said flexible conduit.

24. The process of claim 22 wherein said connector includes a hinged plate section capable of exerting a compressive force on an outer surface of said flexible conduit.

* * * * *